United States Patent

Maccone

Patent Number: 4,853,029
Date of Patent: Aug. 1, 1989

[54] COMPOSITIONS OF METHYL-3-(3'METHYLPHENYL-CARBAMOYLOXY PHENYLCARBAMATE, STABLE IN AN AQUEOUS EMULSION

[75] Inventor: Sergio Maccone, Milan, Italy

[73] Assignee: Agrimont S.p.A., Milan, Italy

[21] Appl. No.: 132,278

[22] Filed: Dec. 14, 1987

[30] Foreign Application Priority Data

Dec. 19, 1986 [IT] Italy ................. 22768 A/86

[51] Int. Cl.[4] .......................... A01N 37/44
[52] U.S. Cl. ...................... 71/111; 71/DIG. 1
[58] Field of Search ................. 71/111, DIG. 1

[56] References Cited

FOREIGN PATENT DOCUMENTS 0102003  3/1984  European Pat. Off. ......... 71/111
1193998  6/1970  United Kingdom ........... 71/111

*Primary Examiner*—Glennon H. Hollrah
*Attorney, Agent, or Firm*—Stevens, Davis, Miller & Mosher

[57] ABSTRACT

Herbicidal compositions, stable in aqueous emulsion, consisting essentially of 15–20% by weight of methyl-3-(3'-methylphenyl-carbamoyloxy)phenylcarbamate, isophorone in amount sufficient ot reach 100%, 3 to 5% by weight of calcium dodecylbenzenesulphonate, and 7–10% by weight of a phosphoric ester of a polyoxyethylated alkylarylphenol having the formula:

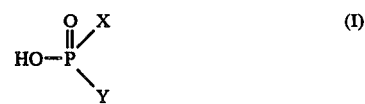

wherein
Y is -OH or X;
X is

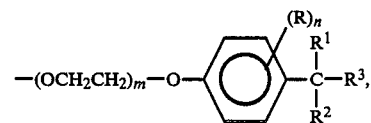

wherein $m = 1-40$;
R is $-CH/CH_3-C_6H_5$, $-CH_2-C_6H_5$, or a $C_4-C_{12}$ alkyl group
$n = 1-4$;
wherein $R^1$ and $R^2$, which may be the same or different, are H or $-CH_3$; and
$R^3$ is

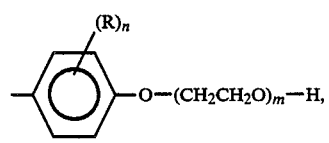

wherein m, R and n have the meanings as specified above, or $CH_3(CH_2)_q-$, wherein $q = 1-20$.

1 Claim, No Drawings

COMPOSITIONS OF METHYL-3-(3'METHYLPHENYL-CARBAMOYLOXY PHENYLCARBAMATE, STABLE IN AN AQUEOUS EMULSION

DESCRIPTION OF THE INVENTION

The present invention relates to herbicidal compositions based on methyl-3-(3'-methylphenylcarbamoyloxy)phenyl carbamate (Phenmedipham, according to the ISO definition), which compositions give rise to stable aqueous emulsions. It is known that Phenmedipham, being very little soluble in water, is formulated at first as a concentrated composition with organic solvents and surfactants, and afterwards such a composition is used to form aqueous emulsions suitable to be distributed uniformly on the cultivations, for instance by nebulization or by spraying by means of mechanical pumps.

The known concentrated compositions of Phenmedipham in organic solvents containing surfactants give rise, however, to aqueous emulsions which are often unstable; namely, they give rise to the formation of crystallization and/or separation of the product in the form of a cream or of an oil.

The presence of crystals or of creamy or oily products in the aqueous emulsions gives rise to dishomogeneities in the herbicidal treatment, and thereby part of the active substance for the weed elimination is not utilized, and to further drawbacks caused by possible clogging of the nozzles of the mechanical distribution pumps.

It has now been discovered that stable aqueous emulsions of Phenmedipham, free from the above-mentioned drawbacks, may be obtained, by using concentrated compositions of Phenmedipham in isophorone, containing particular phosphoric esters of polyoxyethylated alkylarylphenols.

Therefore the present invention relates to herbicidal compositions, stable in an aqueous emulsion, consisting or consisting essentially of 15–20% by weight of methyl-3-(3'-methylphenylcarbamoyloxy)phenyl carbamate, isophorone in amount sufficient to reach 100%, 3–5% by weight of calcium dodecylbenzenesulphonate, and 7–10% by weight of phosphoric esters of polyoxyethylated alkylarylphenols, having the formula:

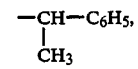

(I)

wherein:
Y is —OH or X;
X is

wherein m—1–40, preferably 1–20;
R is

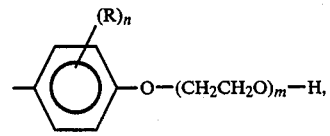

$CH_2$-$C_6H_5$ or a $C_4$-$C_{12}$ alkyl group;
n=1–4, preferably 4;
wherein $R^1$, $R^2$, which may be the same or different, are H or —$CH_3$; and
$R^3$ is

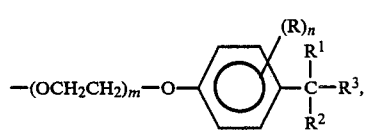

wherein m, R and n have the meanings as defined hereinbefore, or a group of $CH_3(CH_2)_q$—, wherein q=1–20.

Among the phosphoric esters of polyoxyethylated alkylarylphenols having formula (I), the following mixture proved to be particularly suitable, namely the 1:1 mixture of the compound of formula (I) wherein Y=—OH, and of the compound of formula (I) wherein Y is X, in which the index m is 18,
R=

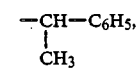

n=4, p=1
$R^1$ and $R^2$ are —$CH_3$, and $R^3$ is

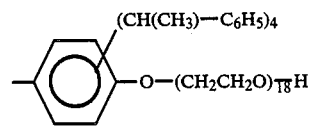

Compounds having the formula (I) are known and can readily be found on the market, both as single compounds and as mixtures.

The preparation of the compositions, according to the present invention, is carried out by mixing the components in predetermined amounts.

The compositions of the present invention give rise to perfectly stable aqueous emulsions, without the formation of crystals and/or the separation of creamy or oily sediments.

The following examples will still better illustrate the invention.

EXAMPLE 1

A composition was prepared, according to the present invention, by dissolving 16.5 g of 97% technical Phenmedipham into 72 g of isophorone and by adding to the solution 3.5 g of calcium dodecylbenzenesulphonate and 8 g of surfactant A, consisting of a 1:1 mixture of the compound of formula (I), wherein Y is —OH and of the compound of formula (I) wherein Y is X, in which index m is 18, R=

$$-\overset{\displaystyle CH_3}{\underset{\displaystyle |}{CH}}-C_6H_5,$$

n=4, p=1, R$^1$ and R$^2$ are —CH$_3$, and R$^3$ is

[structure: phenyl ring with (CH(CH$_3$)—C$_6$H$_5$)$_4$ substituent and —O—(CH$_2$CH$_2$O)$_{18}$H]

The mixture was stirred at room temperature in order to assure homogenity.

The composition thus obtained, expressed in % by weight, is reported in Table 1 as composition 1.

EXAMPLES 2–5

By operating as in Example 1, four comparison compositions were prepared, wherein, instead of surfactant A, use was made of the following surfactants:

Surfactant B=a 1:1 mixture of mono- and di-esters of phosphoric acid with polyoxyethylated nonylphenol (20 ETO).

Surfactant C=a 1:1 mixture of mono- and di-esters of phosphoric acid with polyoxyethylated octylphenol (40 ETO).

Surfactant D=a mixture of phosphoric esters of polyethoxylated allylphenols.

Surfactant E=a mixture of phosphoric esters of polyethoxylated tristyryl- and distyryl-phenols.

The compositions, thus obtained, expressed in % by weight, are reported in Table 1.

TABLE 1

| Components | Compositions Expressed In % By Weight | | | | |
|---|---|---|---|---|---|
| | 1 | 2 | 3 | 4 | 5 |
| Phenmedipham at 97% | 16.5 | 16.5 | 16.5 | 16.5 | 16.5 |
| Isophorone | 72 | 72 | 72 | 72 | 72 |
| Ca dodecylbenzenesulphonate | 3.5 | 3.5 | 3.5 | 3.5 | 3.5 |
| Surfactant A | 8 | — | — | — | — |
| Surfactant B | — | 8 | — | — | — |
| Surfactant C | — | — | 8 | — | — |
| Surfactant D | — | — | 13 | 8 | — |
| Surfactant E | — | — | — | — | 8 |

EXAMPLE 6

Determination of the stability in an aqueous emulsion of compositions 1–5 as reported in Table 1.

For such determination use was made of 5 graduated cylinders having a capacity of 100 ml, equipped with a frosted stopper, each one of them containing 97.5 ml of water, at 30° C., having a standard hardness of 342 p.p.m., expressed as calcium carbonate.

Afterwards 2.5 ml of each one of the compositions 1–5, respectively, were introduced into the cylinders.

Then the cylinders were stoppered and overturned continuously for 30 times over a period of 60 seconds. Then, after having removed the stoppers, the cylinders were permitted to settle in a thermostatically-controlled bath at 30° C. for 8 hours.

At the end of this period of time, creamy separations or sediments and the appearance of crystals were noted in the four cylinders containing compositions 2–5, respectively, whereas no separation or appearance of crystals were noted in the cylinder containing composition No. 1 according to the present invention.

What is claimed is:

1. A herbicidal composition, stable in an aqueous emulsion, consisting essentially of: 15–20% by weight of methyl-3-(3'-methylphenyl-carbamoyloxy)phenyl carbamate, isophorone in amount sufficient to reach 100%, 3 to 5% by weight of calcium dodecylbenzenesulphonate, and 7–10% by weight of phosphoric esters of polyoxyethylated alkylarylphenols having the formula:

$$HO-\underset{\diagdown Y}{\overset{\overset{\displaystyle O}{\|}}{P}}\diagup X \qquad (I)$$

wherein:
Y is —OH or X;
X is

[structure: —(OCH$_2$CH$_2$)$_m$—O—phenyl(R)$_n$—C(R$^1$)(R$^2$)—R$_3$]

m=18, R=

$$-\overset{\displaystyle CH_3}{\underset{\displaystyle |}{CH}}-C_6H_5$$

n=4, R$^1$ and R$^2$=—CH$_3$, R$^3$=

[structure: phenyl ring with (CH(CH$_3$)—C$_6$H$_5$)$_4$ substituent and —O—(CH$_2$CH$_2$O)$_{18}$H]

and further, wherein the phosphoric esters of polyoxyethylated alkylarylphenols are a 1:1 mixture of the compound of formula (I) wherein Y=OH in combination with the compound of formula (I) wherein Y=X.

* * * * *